US009629964B2

United States Patent
Wuepper

(10) Patent No.: US 9,629,964 B2
(45) Date of Patent: Apr. 25, 2017

(54) MOISTURE SENSOR FOR MONITORING AN ACCESS TO A PATIENT AND METHOD OF PRODUCING THE MOISTURE SENSOR

(71) Applicant: Fresenius Medical Care Deutschland GmbH, Bad Homburg v.d.H. (DE)

(72) Inventor: Andreas Wuepper, Buettelborn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/936,931

(22) Filed: Jul. 8, 2013

(65) Prior Publication Data
US 2014/0012198 A1   Jan. 9, 2014

Related U.S. Application Data

(60) Provisional application No. 61/669,162, filed on Jul. 9, 2012.

(30) Foreign Application Priority Data

Jul. 9, 2012   (DE) ........................ 10 2012 013 471

(51) Int. Cl.
*A61M 5/50*   (2006.01)
*G01M 3/16*   (2006.01)
(Continued)

(52) U.S. Cl.
CPC ....... *A61M 5/5086* (2013.01); *A61B 5/02042* (2013.01); *A61M 1/3656* (2014.02);
(Continued)

(58) Field of Classification Search
CPC .............. A61M 5/5086; A61M 1/3653; A61M 1/3656; A61M 2205/15;
(Continued)

(56) References Cited

U.S. PATENT DOCUMENTS 4,298,855 A * 11/1981 Mills ............................... 338/35
6,114,943 A *  9/2000 Lauf ............................... 338/34
(Continued)

FOREIGN PATENT DOCUMENTS

DE   10 2005 017 682 A1   10/2006
DE   10 2009 008 885 A1    8/2010
(Continued)

OTHER PUBLICATIONS

International Search Report, dated Sep. 4, 2013, from corresponding International Application No. PCT/EP2013/001843.
(Continued)

*Primary Examiner* — Hezron E Williams
*Assistant Examiner* — Marrit Eyassu
(74) *Attorney, Agent, or Firm* — Kilyk & Bowersox, P.L.L.C.

(57) ABSTRACT

A moisture sensor for monitoring an access to a patient for a system by which, via a flexible line, a liquid is fed to and/or out from a patient, for monitoring the vascular access in extra-corporeal blood treatment or for monitoring a central venous catheter for acute dialysis, and a method of producing a moisture sensor are described. The moisture sensor has a substrate material with an electrically conductive structure having conductor paths arranged at a distance from one another and connected together across a terminating resistor. The terminating resistor is an electrically conductive film which is applied in a section of the substrate material on which are formed electrical contacting regions for connecting the terminating resistor to the conductor paths, such that an external terminating resistor is not required and the moisture sensor can be produced easily in large numbers complete with the terminating resistor.

12 Claims, 4 Drawing Sheets

(51) Int. Cl.
*A61M 1/36* (2006.01)
*A61B 5/02* (2006.01)
*A61M 5/158* (2006.01)
*G01N 27/04* (2006.01)

(52) U.S. Cl.
CPC ...... *G01M 3/16* (2013.01); *A61M 2005/1588* (2013.01); *A61M 2205/15* (2013.01); *A61M 2205/3317* (2013.01); *G01N 27/048* (2013.01); *Y10T 29/49117* (2015.01)

(58) Field of Classification Search
CPC . A61M 2005/1588; A61M 2205/3317; G01M 3/16; A61B 5/02042; G01N 27/048; Y10T 29/49117
USPC ......................................................... 604/111
See application file for complete search history.

(56) References Cited

U.S. PATENT DOCUMENTS

| | | | | |
|---|---|---|---|---|
| 7,828,019 | B2* | 11/2010 | Shen et al. | ................ 139/383 R |
| 2002/0180578 | A1* | 12/2002 | Sandbach | ....................... 338/99 |
| 2002/0187388 | A1* | 12/2002 | Stumper et al. | ................ 429/44 |
| 2002/0198483 | A1* | 12/2002 | Wariar et al. | ................ 604/5.01 |
| 2005/0038325 | A1* | 2/2005 | Moll | ............................ 600/300 |
| 2008/0202623 | A1* | 8/2008 | DeAngelis et al. | ...... 139/425 R |
| 2010/0081049 | A1 | 4/2010 | Holl et al. | |
| 2010/0271212 | A1* | 10/2010 | Page | ......................... 340/573.1 |
| 2011/0290304 | A1* | 12/2011 | Daniel | ............. H01L 31/03926 136/251 |
| 2012/0029410 | A1 | 2/2012 | Koenig et al. | |
| 2013/0053754 | A1* | 2/2013 | Heppe | ................. A61M 1/3653 604/6.16 |

FOREIGN PATENT DOCUMENTS

| | | | | |
|---|---|---|---|---|
| DE | 10 2010 012 545 A1 | 9/2011 | | |
| DE | 10 2010 023 132 | 12/2011 | | |
| DE | 102010024654 A1 | 12/2011 | | |
| WO | WO 2004004615 A1 * | 1/2004 | ............. A61F 13/42 |
| WO | WO 2005093397 A1 * | 10/2005 | ............. G01N 27/12 |
| WO | 2006/008866 A1 | 1/2006 | | |
| WO | 2010/091852 | 8/2010 | | |
| WO | 2010/091852 A1 | 8/2010 | | |
| WO | 2011/116943 | 9/2011 | | |
| WO | 2011/116943 A1 | 9/2011 | | |
| WO | WO 2011116943 A1 * | 9/2011 | .......... A61M 1/3653 |

OTHER PUBLICATIONS

International Preliminary Report on Patentability (IPRP) dated Jan. 13, 2015 in PCT/EP2013/001843.

* cited by examiner

MOISTURE SENSOR FOR MONITORING AN ACCESS TO A PATIENT AND METHOD OF PRODUCING THE MOISTURE SENSOR

CROSS REFERENCE TO RELATED APPLICATIONS

The present application claims priority to U.S. Provisional Patent Application Ser. No. 61/669,162, filed on Jul. 9, 2012, and Application No. DE 10 2012 013 471.1, filed in the Federal Republic of Germany on Jul. 9, 2012, each of which is expressly incorporated herein in its entirety by reference thereto.

FIELD OF INVENTION

The present invention relates to a moisture sensor for monitoring an access to a patient for a system by which, via a flexible line, a liquid is fed to a patient and/or a liquid is fed out from the patient, and in particular for monitoring the vascular access in extra-corporeal blood treatment. As well as this, the present invention also relates to a method of producing a moisture sensor for monitoring an access to a patient.

BACKGROUND INFORMATION

In the field of medical engineering, there are various known systems with which, via a flexible line, liquids can be withdrawn from patients or liquids can be fed to patients. The access to the patients is generally gained in this case by means of a catheter for insertion in organs of the body or by means of a needle for puncturing vessels. During the examination or treatment, it has to be ensured that proper access exists to the patient. It is therefore necessary for the patient access to be monitored.

Proper access to the patient is also a particular prerequisite for the pieces of extra-corporeal blood treatment apparatus which have an extra-corporeal blood circuit. The known pieces of extra-corporeal blood treatment apparatus include for example pieces of dialysis apparatus and cell separators which require access to the patient's vascular system. In extra-corporeal blood treatment, blood is withdrawn from the patient along a flexible arterial line having an arterial puncturing needle and is fed back to the patient along a flexible venous line having a venous puncturing needle. In acute dialysis at intensive care stations on the other hand, what is used as a patient access is a central venous catheter in the patient's neck.

There are various known arrangements of different forms for monitoring the vascular access. These known monitoring arrangements generally rely on the safety devices which are provided as standard in the pieces of blood treatment apparatus and which trigger an immediate shutoff of the extra-corporeal blood circuit if there is not a proper vascular access.

There are known arrangements for monitoring a vascular access which have a device for detecting moisture to enable the escape of blood to be detected at the site of the puncture. These known moisture sensors take the form of a pad which has to be applied to the site of the puncture and which consists of an absorbent material to which an electrically conductive structure is applied or in which an electrically conductive structure is embedded. The electrically conductive structure comprises conductor paths arranged at a distance from one another which are arranged on or in the substrate material. Wetting of the substrate material by a liquid results in a change in the resistance between the conductor paths.

The known moisture sensors are connected by a connecting line to an arrangement which senses a change in the resistance between the conductor paths.

An electrically conductive structure which comprises two conductor paths open at the ends which are arranged at a distance from one another is a disadvantage in that the sensing arrangement is not able to detect either any damage to the conductor paths or a misconnection of the moisture sensor, because a break in a conductor path or the connecting line or the making of a faulty contact at the connection does not cause a change in resistance. It is therefore known for the ends of the two conductor paths to be connected together across a terminating resistor. If the resistance of the moisture sensor which is measured by the sensing arrangement corresponds to the resistance of the terminating resistor across the conductor paths, it can be assumed that the moisture sensor is intact and is correctly connected to the sensing arrangement.

There are known moisture sensors which consist of different substrate materials. Textile materials for example are used as substrate materials. The application of the terminating resistor to the substrate material is found to be problem in production. There are therefore known moisture sensors which do not have a terminating resistor but which are connected to an external terminating resistor. However, it is costly and complicated to connect up external terminating resistors.

International Patent Publication No. WO 2011/116943 describes a moisture sensor which takes the form of a woven material comprising non-conductive warp filaments and non-conductive weft filaments and conductive warp filaments and conductive weft filaments, which are so arranged that they form an electrically conductive structure which comprises a first and a second conductor path. The ends of the two conductor paths take the form of connecting contacts which are arranged on a tongue with a lateral offset from one another. The connector of a connecting cable by which the moisture sensor is electrically connected to the sensing arrangement is connected to the tongue. The sensing arrangement measures the electrical resistance between one pair of connecting contacts of the moisture sensor while the other pair of connecting contacts are connected together across a terminating resistor which is incorporated in the connector.

A moisture sensor which comprises an arrangement of conductor paths arranged on a substrate layer is described in German Application No. DE 10 2010 023 132. The two conductor paths of the moisture sensor are connected together by a contact layer whose resistance changes in the wetted state.

International Patent Publication No. WO 2010/091852 described a moisture sensor in which the conductor path structure and the terminating resistor are applied to a substrate material by screen printing. A printing paste containing silver is used for the conductor path structure and a printing paste containing carbon for the resistor structure. Although it is fundamentally possible for the terminating resistor to be applied by printing even in the case of a moisture sensor made of a textile material, it is found to be a disadvantage because of the additional steps in the procedure which are called for by the printing process.

SUMMARY

An object underlying the present invention is to provide a moisture sensor for monitoring a patient access which can be inexpensively produced in large numbers. It is also an object of the present invention to specify a method of producing the moisture sensor inexpensively in large numbers.

The moisture sensor according to the present invention has a substrate material to be applied to the patient's skin which has an electrically conductive structure which comprises conductor paths arranged at a distance from one another which are connected together across a terminating resistor. The substrate material of the moisture sensor according to the present invention may be different kinds. It may be a textile material or a non-textile material. However, the substrate material should preferably be absorbent.

The moisture sensor according to the present invention is characterised in that the resistor is an electrically conductive film which is applied in a section of the substrate material on which are formed electrical contacting regions for connecting the terminating resistor to the conductor paths. The electrical contacting regions for connecting the terminating resistor may be provided on the underside of the moisture sensor adjacent the patient or on the upper side thereof remote from the patient. The contacting regions do however have to be provided on the same side to enable the electrically conductive film to be applied.

The moisture sensor according to the present invention has the advantage that an external terminating resistor is not required. This simplifies the connecting up of the moisture sensor. The moisture sensor according to the present invention can be easily produced in large numbers complete with the terminating resistor by applying the conductive film as a web of film during the production process. The web of film having been applied, the moisture sensors can be separated out, complete with the terminating resistor, by cutting, punching or stamping the moisture sensors, complete with the terminating resistor, out of the web of material they form together.

The advantages of the moisture sensor according to the present invention become particularly apparent when the substrate material is a textile material, and in particular a woven material, to which it is difficult to apply pasty substances to form the terminating resistor.

In a preferred exemplary embodiment which allows the method of production to be carried out particularly easily, the electrically conductive film and the substrate material are adhesive bonded together by an electrically conductive adhesive. Electrically conductive films and electrically conductive adhesives are part of the prior art.

Rather than their being adhesive bonded by a conductive adhesive, an alternative exemplary embodiment envisages the electrically conductive film and the substrate material being connected by a covering film which extends over the electrically conductive film and which is applied to the substrate material. In this alternative exemplary embodiment the connection of the covering film and the substrate material does not call for the use of an electrically conductive adhesive.

The electrically conductive structure may take different forms. In a preferred exemplary embodiment, the electrically conductive structure has a first conductor path and a second conductor path, with the electrical contacting portions for the connection of the terminating resistor being formed at one end of the first conductor path and one end of the second conductor path. The other end of the first conductor path and the other end of the second conductor path preferably take the form of electrical connecting contacts for an electrical connector for connecting the moisture sensor to the sensing arrangement. The electrical contacting portions for the terminating resistor are preferably arranged on one side of the substrate material and the electrical connecting contacts for the connector are preferably arranged on the other side thereof. This makes it possible for the terminating resistor to be produced by applying the electrically conductive film to the side of the moisture sensor which has the contacting portions.

The substrate material of the moisture sensor preferably takes the form of a planar material, with the electrical contacting portions and the electrical connecting contacts being arranged on a tongue belonging to the planar material. The tongue on the one hand allows the connector to be connected easily and on the other hand allows the electrically conductive film to be applied because the tongue is physically separated from the electrically conductive structure.

A particularly preferred exemplary embodiment makes provision for a substrate material of non-conductive warp filaments and non-conductive weft filaments and conductive warp filaments and conductive weft filaments, the electrically conductive structure being formed by conductive warp filaments and/or weft filaments. The advantages of the moisture sensor according to the present invention are particularly apparent in this exemplary embodiment because the web of conductive film can easily be connected to the web of woven material. The electrically conductive film may be any film which has a suitable resistance. What are suitable as electrically conductive films are for example the known carbon films or polymer films.

The value of the terminating resistor should be more than the resistance of the wetted moisture sensor and less than the value of the internal resistance of the sensing arrangement including the resistance of the connecting cable. If the sensor is to respond to single drops of liquid regardless of the relative humidity of the surroundings, a value of 100 kohms to 1000 kohms has been found to be advantageous for the terminating resistor in practice.

The method of producing the moisture sensor is characterised in that, in the first step of the method, a web of woven material is woven from non-conductive warp filaments and non-conductive weft filaments and conductive warp filaments and conductive weft filaments, the conductive and non-conductive warp and weft filaments being so arranged that the said conductive and non-conductive warp and weft filaments form an electrically conductive structure in the woven material. A method of weaving of this kind is part of the prior art. This method of weaving is described in International Patent Publication No. WO 2011/116943.

Only one additional step of the method, to produce the terminating resistor, follows the weaving process, this step being easily able to be incorporated into the production process. In this step of the method, a web of an electrically conductive film, which is preferably a self-adhesive film, is applied to the web of woven material. The width of the web of film is smaller in this case than the width of the web of woven material, the web of film being applied to that section of the substrate material on which the electrical contacting portions for the terminating resistor are formed. The individual moisture sensors are then separated out by cutting, punching or stamping the sensors out from the web of material to the preset outline. The method according to the present invention may also comprise further steps which include for example washing, impregnation, application of a layer for adhesion, and covering with a backing layer, such as for example siliconised paper, and the like.

Exemplary embodiments of the present invention are explained in detail below with reference to the accompanying drawings.

DETAILED DESCRIPTION

Figure 1:
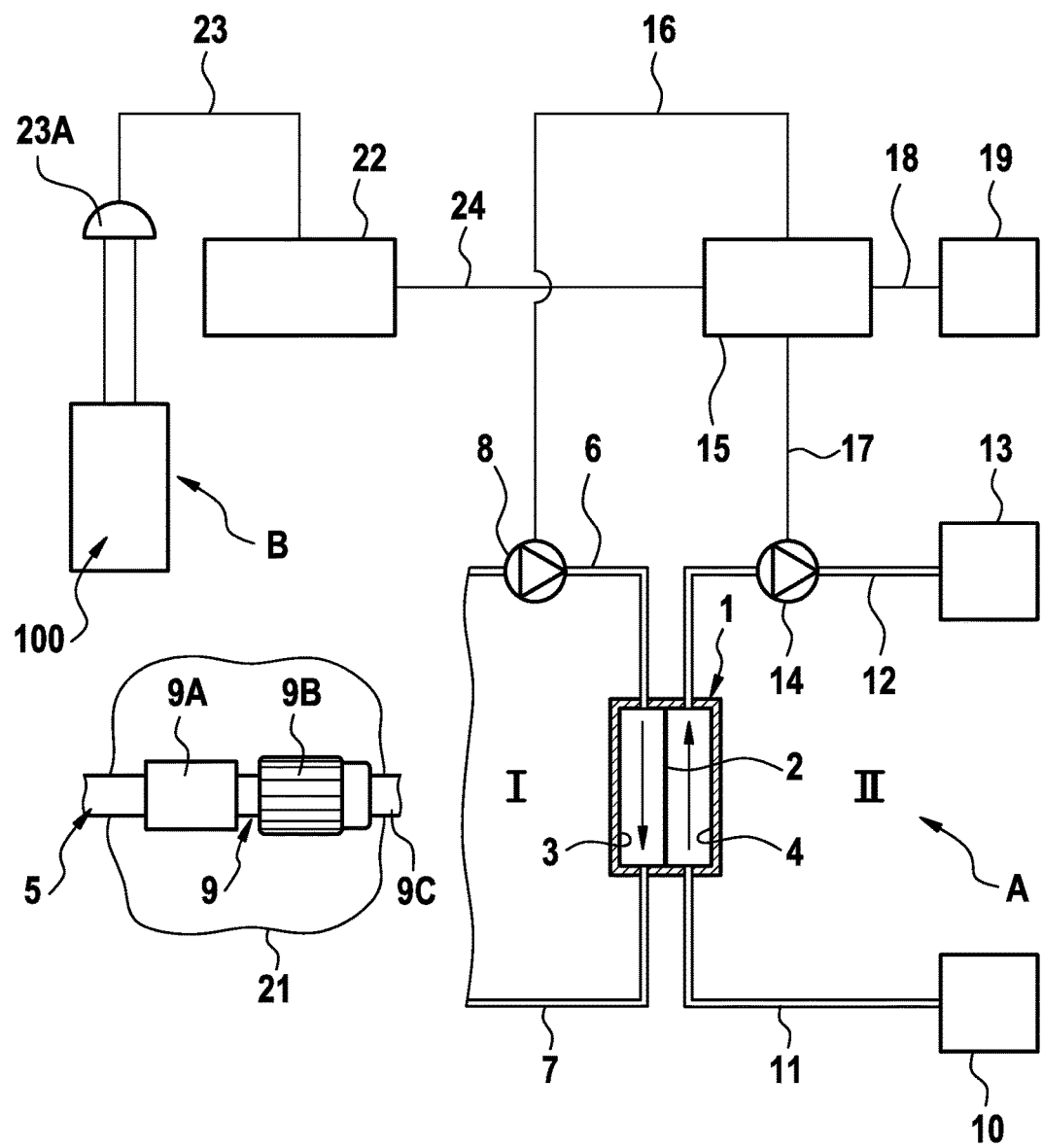
FIG. 1 shows the principal components of a blood treatment apparatus which has an arrangement for monitoring a vascular access.

FIG. 1 shows the principal components of a blood treatment apparatus, and in particular a haemodialysis apparatus A for acute dialysis, which has an arrangement B for monitoring a vascular access and in particular a vascular access which has a central venous catheter. The monitoring arrangement B is part of the haemodialysis apparatus A in the present exemplary embodiment. The dialysis apparatus will first be described with reference to FIG. 1.

The haemodialysis apparatus A has a dialyser 1 which is divided into a blood chamber 3 and a dialysis-fluid chamber 4 by a semi-permeable membrane 2. The vascular access to the patient is obtained by means of a central venous catheter 5 which is connected to the patient's neck. The central venous catheter 5 is part of the extra-corporeal blood circuit I, which is merely indicated and which includes the blood chamber 3 of the dialyser 1 and comprises flexible lines 6, 7. A blood pump 8 is provided to pump the blood in the extra-corporeal circuit.

The dialysis-fluid circuit II of the dialysis apparatus A comprises a dialysis-fluid source 10 to which a dialysis-fluid infeed line 11, which runs to the inlet of the dialysis-fluid chamber 4 of the dialyser 1, is connected. Running off from the outlet of the dialysis-fluid chamber 4 of the dialyser 1 is a dialysis-fluid outfeed line 12 which runs to an outlet 13. A dialysis-fluid pump 14 is connected into the dialysis-fluid outfeed line 12.

Responsible for controlling the dialysis apparatus is a central control unit 15 which operates the blood and dialysis-fluid pumps 8, 14 via control lines 16, 17. The central control unit 15 is connected by a data line 18 to an alarm unit 19 which gives a visual and/or audio and/or tactile alarm if anything untoward happens.

In the present exemplary embodiment, the monitoring arrangement B, which is only shown schematically, is used to monitor a Luer lock connector 9 having parts 9A and 9B, for connecting the central venous catheter 5 to a flexible line 9C belonging to the extra-corporeal blood circuit I. The monitoring arrangement B has a device 100 for detecting moisture which is arranged at the point 21 of the connection to the flexible line. This moisture sensor 100 is only shown in schematic form in FIG. 1. As well as this, the monitoring arrangement B also has a sensing arrangement 22 which is electrically connected to the moisture sensor 100 by a connecting line 23. The connecting line 23 is connected to the moisture sensor 100 by an electrical connector 23A.

The sensing arrangement 22 is connected to the central control unit 15 of the dialysis apparatus A by a data line 24. In the event of blood escaping from the point of connection 21 to the flexible line and wetting the moisture sensor 100, the sensing arrangement 22 of the monitoring arrangement B generates a control signal which the central control unit 15 receives via the data line 24, the central control unit 15 then making an intervention in the blood treatment. The control unit 15 stops the blood pump 8 and generates an alarm signal so that the alarm unit 19 gives an audio and/or visual and/or tactile alarm.

The moisture sensor 100 according to the present invention will be described in detail herein. As a substrate, the moisture sensor has a multi-ply woven material which comprises electrically conductive and electrically non-conductive warp and weft filaments (e.g., monofilaments, carbon fibres, silver coated polyamide yarns). The moisture sensor 100 has an underside adjacent the patient's skin and an upper side remote from the patient's skin. It has a central region 100A to which are connected a left-hand and a right-hand arm 100B, 100C, respectively, which extend round a circular cut-out 100D. Connected to the central region 100A on the opposite side from the arms is a connecting tongue 100E.

Figure 2:
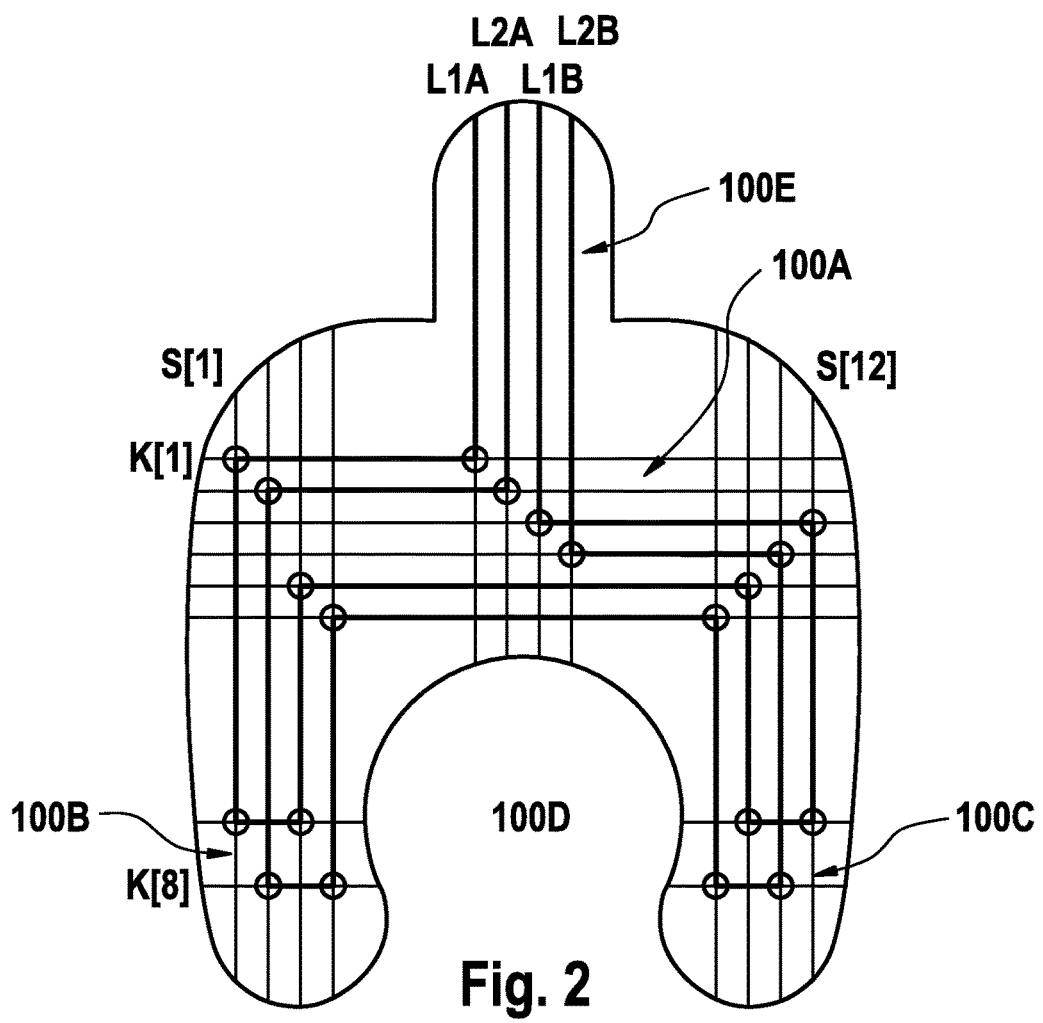
FIG. 2 is a schematic view of the moisture sensor having the electrically conductive structure.

The electrically conductive and electrically non-conductive warp and weft filaments are so arranged in the multi-ply woven material that an electrically conductive structure is formed. The electrically conductive structure comprises warp and weft filaments extending orthogonally to one another which are electrically conductive. In FIG. 2, the electrically conductive warp and weft filaments are identified as K[1] to K[8] and S[1] to S[12] respectively. The intersections of the warp and weft filaments are indicated in FIG. 2 by circles. The moisture sensor shown in FIG. 2 is a preferred exemplary embodiment for monitoring the venous and/or arterial needles in chronic haemodialysis.

The electrically conductive structure L1, L2 comprises two conductor paths L1 and L2. The start of each conductor path is identified as "A" and the ends of the conductor paths as "B". The first conductor path L1 extends from the connecting tongue 100E over the central region 100A to the left-hand arm 100B, from the left-hand arm over the central region to the right-hand arm 100C, and from the right-hand arm over the central region back again to the tongue 100E. The second conductor path L2 extends from the tongue 100E over the central region 100A to the left-hand arm 100B, from the left-hand arm 100B over the central region to the right-hand arm 100C, and from the right-hand arm over the central region to the tongue 100E. The two conductor paths L1 and L2 extend parallel to and at a distance from one another. They each have a plurality of portions which are positioned orthogonally to one another.

Figure 3A:
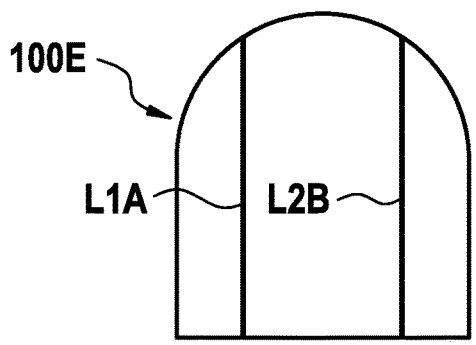
FIG. 3A is a plan view of a first exemplary embodiment of the connecting tongue of the moisture sensor.
Figure 3B:
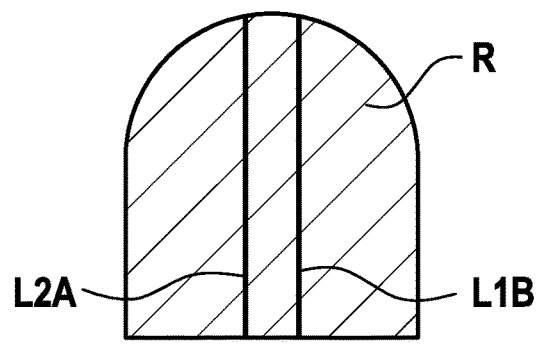
FIG. 3B is a view from below of the connecting tongue shown in FIG. 3A.

One end L1A and L2B of the first and second conductor paths L1, L2 form two outer connecting contacts on the upper side of the tongue 100E (FIG. 3A), whereas the other ends L1B and L2A of the first and second conductor paths L1, L2 form two inner contacting portions on the underside of the tongue 100E (FIG. 3B). These contacting portions are shown schematically in FIGS. 3A and 3B.

The two inner contacting portions L1B and L2A are electrically connected to a terminating resistor R which is not shown in the drawings. The terminating resistor R is a conductive film which is applied to the upper side or underside of the tongue 100E.

In the exemplary embodiment, the electrically conductive film R by which the contacting portions L2A and L1B of the conductor paths L1, L2 are connected together is applied to the underside of the tongue 100E. This film is indicated by single hatching in FIG. 3B.

Figure 4A:
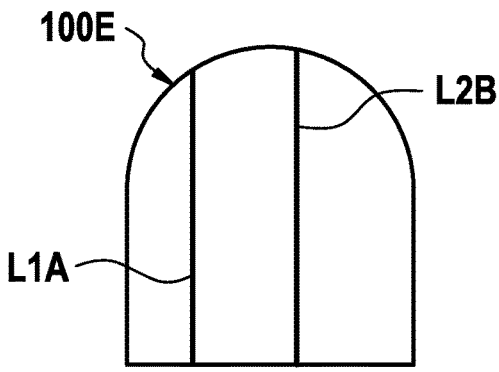
FIG. 4A is a plan view of a second exemplary embodiment of connecting tongue.
Figure 4B:
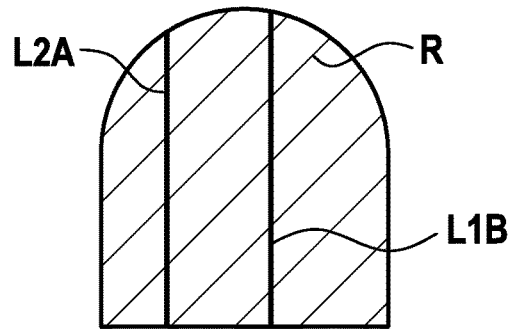
FIG. 4B is a view from below of the connecting tongue shown in FIG. 4A.

FIGS. 4A and 4B show the upper side and underside of a second exemplary embodiment of the tongue 100E which differs from the first exemplary embodiment in the arrangement of the contacting portions and connecting contacts on the upper side and underside of the tongue, there being an outer and an inner connecting contact L1A, L2B (FIG. 4A) situated on the upper side of the tongue 100E and an outer and an inner contacting portion L2A, L1B situated on the underside of the tongue (FIG. 4B). In this exemplary embodiment, the conductive film R is applied to the underside of the tongue 100E, which has the contacting portions L2A, L1B (FIG. 4B). The conductive film R is once again indicated by single hatched lines.

Figure 5:
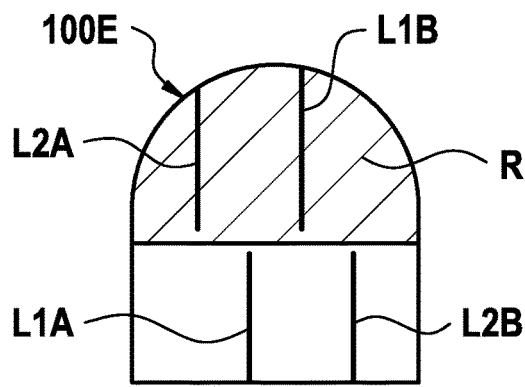
FIG. 5 is a plan view of a third exemplary embodiment of the connecting tongue.

FIG. 5 shows a further exemplary embodiment of the tongue 100E in which the two connecting contacts and the two contacting portions are situated only on the upper side of the tongue 100E. The connecting contacts L1A, L2B are for example situated on the inner side adjacent the central portion 100A and the contacting portions L2A, L1B on the outer side of the tongue, the connecting contacts and contacting portions being offset from one another laterally. In this exemplary embodiment, the conductive film R is applied to the upper side of the connecting tongue 100E, the film extending however only over the outer half of the connecting tongue in which the contacting portions L2A, L1B are situated. The conductive film R is indicated by single hatched lines.

Figure 6:
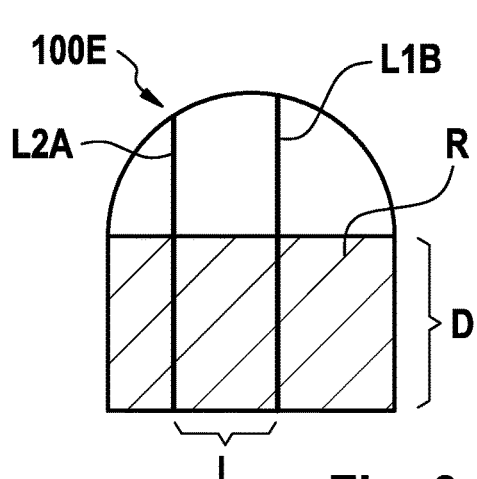
FIG. 6 shows an exemplary embodiment of the connecting tongue of the moisture sensor together with a first exemplary embodiment of the terminating resistor.

FIG. 6 shows the contacting portions L2A, L1B on the upper side of a tongue 100E which are connected together electrically by the electrically conductive film R. The electrically conductive film R extends only over the bottom half of the connecting tongue. The distance between the parallel contacting portions L2A, L1B in line form is identified as L and the width of the conductive film R as D. With a given sheet resistance for the film, the resistance $R_O$ of the terminating resistor R can be set within certain limits by the distance L between the contacting portions and the width D of the film. With a given sheet resistance for the film, the resistance $R_O$ is proportional to the distance L and inversely proportional to the width D. The conductive film R is once again indicated by single hatched lines.

The resistance $R_O$ of the terminating resistor should be between 100 kohms and 1000 kohms. This gives a sheet resistance for the electrically conductive film which is between $2\times10^4$ ohm/sq and $5\times10^7$ ohm/sq. This value corresponds to the sheet resistance of known electrically conductive polymer films (e.g., dissipative polymers). It is however also possible for known electrically conductive carbon films which are used for protection against electrostatic charges to be used as the terminating resistor.

Figure 7:
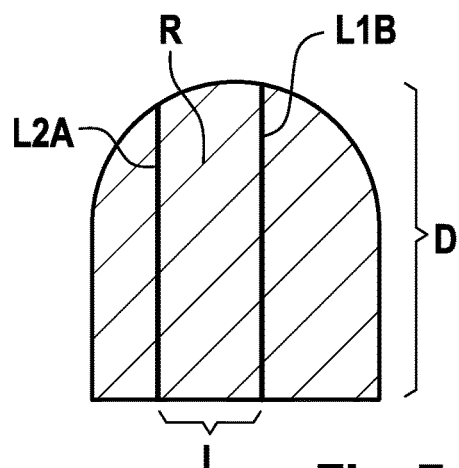
FIG. 7 shows the connecting tongue shown in FIG. 6 together with a second exemplary embodiment of the terminating resistor.

In a preferred exemplary embodiment, the electrically conductive films are adhesive bonded to the connecting tongue 100E of the moisture sensor 1 by an electrically conductive adhesive, in which case the film may cover a part of the tongue or its entire area. FIG. 7 shows an exemplary embodiment in which the electrically conductive film R covers the entire area of the tongue 100E of the moisture sensor.

Figure 8:
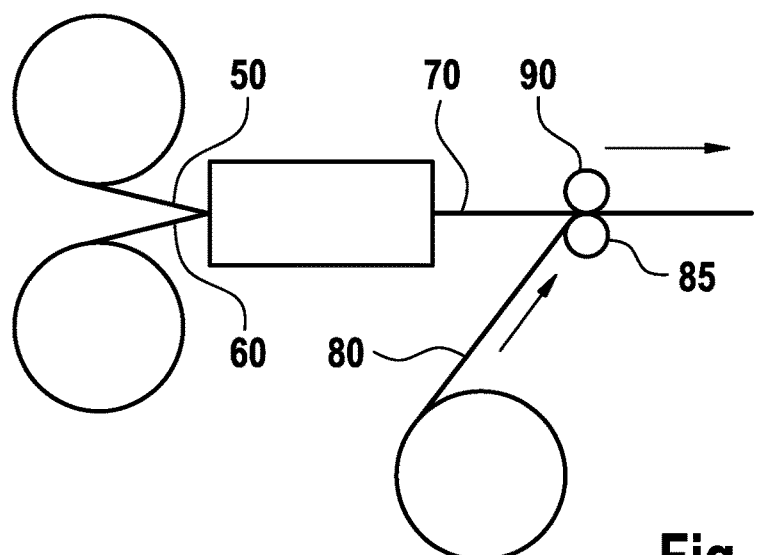
FIG. 8 is a view of the principal steps in the method of producing the moisture sensor according to the present invention.

FIG. 8 is a schematic view of the method step comprising the production of the web of woven material 70 from warp and weft filaments 50, 60, on which web of woven material 70 are situated a plurality of moisture sensors laid out in columns and rows which each have an electrically conductive structure. In a step of the method which follows the weaving process, a web 80 made of an electrically conductive film is applied to the upper side or underside of the tongues, the woven material and film being adhesive bonded together by an electrically conductive adhesive. The web of woven material is applied to the upper side or underside of that region of the tongue on which the connecting portions for connecting to the terminating resistor are situated. To apply the web of film 80 to the web of woven material 70, the film and the web of woven material pass through two pressure-applying rollers 85, 90 by which the requisite applied pressure is exerted on the webs.

Figure 9:
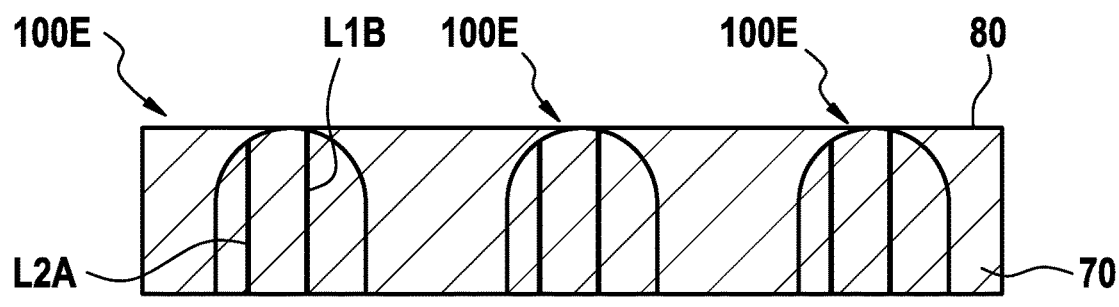
FIG. 9 is a view of the step of the method which comprises the application of the terminating resistor to the moisture sensor.

FIG. 9 is a schematic view of that part of the web of woven material 70 in which the web of film 80 is applied to the upper side of the web of woven material. The web of film 80 indicated by the single hatched lines covers the entire area of the upper side of the tongues 100E which have the contacting portions L2A, L1B. The direction of revolution of the pressure-applying rollers (not shown) between which the webs run is indicated by an arrow.

The webs of film and woven material 70, 80 having been bonded together, the moisture sensors are cut, punched or stamped out, in order then to be finished and packed. The method of production comprises other steps which are known to the person skilled in the art but are not shown in FIG. 8.

Figure 10:
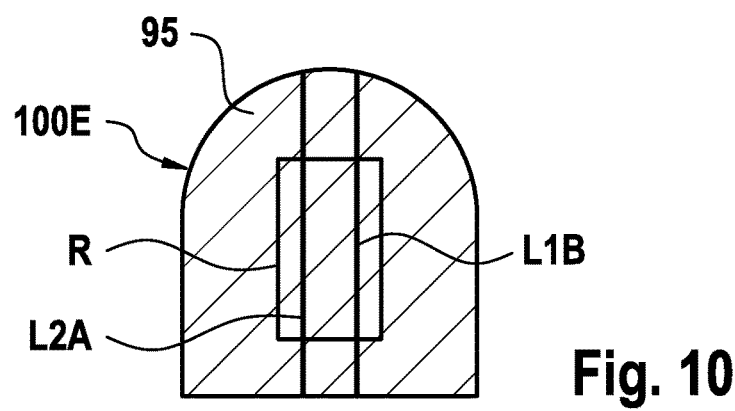
FIG. 10 shows an alternative exemplary embodiment of the connecting tongue of the moisture sensor.

FIG. 10 shows an alternative exemplary embodiment of the connecting tongue 100E of the moisture sensor in which a woven material and a film are adhesive bonded together by an electrically conductive adhesive. In this exemplary embodiment, the electrically conductive film R lies only on the contacting portions L2A, L1B. The electrically conductive film R is fixed in place by a covering film 95 which extends beyond the edges of the electrically conductive film R. On the underside, the covering film 95 is provided with an adhesive or adhering layer, thus causing the covering film to adhere to the tongue 100E to fix the electrically conductive film in place.

What is claimed is:

1. A moisture sensor for monitoring an access to a patient for a system by which, via a flexible line, a liquid is fed at least one of to the patient or from the patient, or for monitoring a vascular access in extra-corporeal blood treatment, the moisture sensor comprising:
   a substrate material to be applied to the patient's skin, the substrate material including an electrically conductive structure,
   wherein the substrate material has a narrowing extension that forms a connection section, wherein the electrically conductive structure has at least a first and a second conductor path, the at least first and second conductor paths being arranged at a distance from one another, wherein the at least first and second conductor paths each have one end forming an electrical contacting portion and another end forming an electrical connecting contact, wherein the electrical contacting portions are connected together across a terminating resistor, wherein the electrical connecting contacts form an electrical connection for the moisture sensor, wherein the terminating resistor is an electrically conductive film applied to the connection section, wherein the electrically conductive film extends over the connection section where the electrical contacting portions are situated, and the electrically conductive film lies on the electrical contacting portions, wherein the electrical contacting portions and the electrical connecting contacts are located on the narrowing extension that forms the connection section, and wherein the electrically conductive film and the substrate material are adhesively bonded together by a conductive adhesive.

2. The moisture sensor according to claim 1, further comprising:

a covering film extending over and applied to the electrically conductive film, the covering film and the substrate material being adhesively bonded together.

3. The moisture sensor according to claim 1, wherein the electrical contacting portions are arranged on one side of the connection section of the substrate material and the electrical connecting contacts are arranged on another side of the connection section of the substrate material.

4. The moisture sensor according to claim 1, wherein the substrate material is a planar material.

5. The moisture sensor according to claim 1, wherein the substrate material is a textile planar material in which the electrically conductive structure is embedded.

6. The moisture sensor according to claim 1, wherein the substrate material is a woven textile material of non-conductive warp filaments, non-conductive weft filaments, conductive warp filaments and conductive weft filaments, the electrically conductive structure being formed by the conductive warp filaments and/or the conductive weft filaments.

7. The moisture sensor according to claim 1, wherein the conductor paths are laid out in a plurality of portions extending orthogonally to one another and situated next to one another.

8. The moisture sensor according to claim 1, wherein the electrically conductive film is a carbon film or a polymer film.

9. The moisture sensor according to claim 1, wherein a resistance of the terminating resistor is between 100 kohms and 1000 kohms.

10. A method of producing the moisture sensor according to claim 1, the method comprising:

weaving a web of woven material from non-conductive warp filaments, nonconductive weft filaments, conductive warp filaments and conductive weft filaments, the conductive and non-conductive warp and weft filaments being arranged such that the conductive and non-conductive warp and weft filaments form an electrically conductive structure in the substrate material;

applying a web of an electrically conductive film, the web of film being a self-adhesive film, to a narrowing extension of the substrate material on which electrical contacting portions for connecting the terminating resistor are formed and electrical connecting contacts for an electrical connection for the moisture sensor are formed, a width of the web of film being smaller than a width of the web of woven material; and separating out individual moisture sensors.

11. The method according to claim 10, wherein the web of film and the web of woven material extend between two pressure-applying rollers during application of the web of film to the web of woven material.

12. The moisture sensor according to claim 1, wherein the substrate material includes (1) the connection section, (2) a first arm and (3) a second arm; and wherein the at least first and second conductor paths traverse each of the connection section, the first arm and the second arm.

* * * * *